United States Patent
Lok

(10) Patent No.: US 7,125,973 B2
(45) Date of Patent: Oct. 24, 2006

(54) CELL SURFACE DISPLAY OF PROTEINS BY RECOMBINANT HOST CELLS

(75) Inventor: Si Lok, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 10/693,587

(22) Filed: Oct. 24, 2003

(65) Prior Publication Data

US 2004/0063141 A1 Apr. 1, 2004

Related U.S. Application Data

(62) Division of application No. 09/704,090, filed on Nov. 1, 2000, now Pat. No. 6,686,168.

(60) Provisional application No. 60/163,501, filed on Nov. 4, 1999.

(51) Int. Cl.
*C07H 21/04* (2006.01)
*C12N 15/11* (2006.01)
*C12N 5/10* (2006.01)

(52) U.S. Cl. .................. 536/23.1; 435/320.1; 435/325

(58) Field of Classification Search .................... 435/6, 435/69.1, 320.1; 530/350
See application file for complete search history.

(56) References Cited

U.S. PATENT DOCUMENTS 6,686,168 B1 * 2/2004 Lok .......................... 435/7.21

FOREIGN PATENT DOCUMENTS

WO WO98/39476 * 11/1998

OTHER PUBLICATIONS

Hamann, J. et al., "AICL: a new activation-induced antigen encoded by the human NK gene complex", 1997, Immunogenetics, vol. 45: pp. 295-300.*
Yokoyama-Kobayashi, M., et al. "Selection of cDNAs encoding putative type II membrane proteins on the cell surface from a human full-length cDNA bank", 1999, Gene, vol. 228: pp. 161-167.*
Yokoyama-Kobayashi, M., et al. "Signal sequence detection system using secreted protease activity as an indicator", 1995, Gene, vol. 163, pp. 193-196.*

* cited by examiner

*Primary Examiner*—David Guzo
*Assistant Examiner*—Michael D. Burkhart
(74) *Attorney, Agent, or Firm*—Shelby J. Walker

(57) ABSTRACT

Methods and vectors are described for expressing recombinant proteins on the surface of host cells. These processes and compositions provide the basis for strategies to produce a fusion protein, comprising a membrane anchor that allows extracellular attachment of the fusion protein in a type II orientation.

22 Claims, 3 Drawing Sheets ns. In this

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Peptide spacer.

<400> SEQUENCE: 1

Gly Gly Gly Gly Ala Ala Gly Gly Gly Gly Ala Ala
 1               5                  10

<210> SEQ ID NO 2
<211> LENGTH: 26
<212> TYPE: PRT
<213> ORGANISM: Artificial Sequence
<220> FEATURE:
<223> OTHER INFORMATION: Transmembrane domain

<400> SEQUENCE: 2

Leu Phe Leu Ser Leu Phe Ser Phe Leu Ile Val Ala Gly Ala Thr Thr
 1               5                  10                  15

Leu Phe Cys Leu Leu His Phe Gly Val Ile
            20                  25

<210> SEQ ID NO 3
<211> LENGTH: 30
<212> TYPE: PRT
<213> ORGANISM: Artificial Sequence
<220> FEATURE:
<223> OTHER INFORMATION: N-terminal sequence

<400> SEQUENCE: 3

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys
            20                  25                  30

<210> SEQ ID NO 4
<211> LENGTH: 10
<212> TYPE: PRT
<213> ORGANISM: Artificial Sequence
<220> FEATURE:
<223> OTHER INFORMATION: c-Myc tag

<400> SEQUENCE: 4

Glu Gln Lys Leu Ile Ser Glu Glu Asp Leu
 1               5                  10

<210> SEQ ID NO 5
<211> LENGTH: 9
<212> TYPE: PRT
<213> ORGANISM: Artificial Sequence
```

```
<220> FEATURE:
<223> OTHER INFORMATION: Hemagglutinin A epitope tag

<400> SEQUENCE: 5

Tyr Pro Tyr Asp Val Pro Asp Tyr Ala
1               5
```

CELL SURFACE DISPLAY OF PROTEINS BY RECOMBINANT HOST CELLS

CROSS-REFERENCE TO RELATED APPLICATIONS

This application is a divisional of U.S. patent application Ser. No. 09/704,090, filed Nov. 1, 2000, now U.S. Pat. No. 6,686,168, issued Feb. 3, 2004, which claims the benefit of U.S. Provisional Application No. 60/163,501, filed Nov. 4, 1999, both of which are incorporated by reference.

TECHNICAL FIELD

The present invention relates generally to methods for expressing recombinant proteins on the surface of host cells. In particular, the present invention relates to strategies for producing a fusion protein comprising a membrane anchor that allows extracellular attachment of the fusion protein in a type II orientation.

BACKGROUND OF THE INVENTION

The expression of foreign proteins on the surface of cells and virus particles provides a powerful tool for such diverse activities as obtaining specific antibodies, determining enzyme specificity, exploring protein-protein interactions, and introducing new functions into proteins. Surface display technology is also used for expression cloning, in which the biological function of a cloned gene product is used for selection.

A number of methods have been devised to display peptides and proteins on the surfaces of bacteria and bacteriophages. The surface display of heterologous protein in bacteria has been implemented for various purposes, such as the production of live bacterial vaccine delivery systems (see, for example, Georgiou et al., U.S. Pat. No. 5,348,867; Huang et al., U.S. Pat. No. 5,516,637; Ståhl and Uhlén, *Trends Biotechnol.* 15:185 (1995)). Bacterial surface display has been achieved using chimeric genes derived from bacterial outer membrane proteins, lipoproteins, fimbria proteins, and flagellar proteins. Bacteriophage display of foreign peptides and proteins has become a powerful tool for generating antigens, identifying peptide ligands, mapping enzyme substrate sites, isolation of high affinity antibodies, and the directed evolution of proteins (see, for example, Phizicky and Fields, *Microbiol. Rev.* 59:94 (1995); Kay et al., *Phage Display of Peptides and Proteins* (Academic Press 1996); Lowman, *Annu. Rev. Biophys. Biomol. Struct.* 26:401 (1997)).

Either bacterial or bacteriophage surface display systems can be used for expression screening. Both approaches, however, share certain drawbacks for expressing eukaryotic proteins. Prokaryotic cells do not efficiently express functional eukaryotic proteins, and these cells lack the ability to introduce post-translational modifications, including glycosylation. Moreover, bacterial and bacteriophage display systems are limited by the small capacity of the display system, and as such, are more suited for the display of small peptides.

There are a limited number of reports on the eukaryotic cell surface display of heterologous proteins. Boder and Wittrup, *Nature Biotechnol.* 15:553 (1997), have described a library screening system using *Saccharomyces cerevisiae* as the displaying particle. This yeast surface display method uses the α-agglutinin yeast adhesion receptor, which consists of two subunits, Aga1 and Aga2. The Aga1 subunit is anchored to the cell wall via a β-glucan covalent linkage, and Aga2 is linked to Aga1 by disulfide bonds. In this approach, recombinant yeast are produced that express Aga1 and an Aga2 fusion protein comprising a foreign polypeptide at the C-terminus of Aga2. Aga1 and the fusion protein associate within the secretory pathway of the yeast cell, and are expressed on the cell surface as a display scaffold.

Various approaches in eukaryotic systems achieve surface display by producing fusion proteins that contain the polypeptide of interest and a transmembrane domain from another protein to anchor the fusion protein to the cell membrane. In eukaryotic cells, the majority of secreted proteins and membrane-bound proteins are translocated across an endoplasmic reticulum membrane concurrently with translation (Wicker and Lodish, *Science* 230:400 (1985); Verner and Schatz, *Science* 241:1307 (1988); Hartmann et al., *Proc. Nat'l Acad. Sci. USA* 86:5786 (1989); Matlack et al., *Cell* 92:381 (1998)). In the first step of this co-translocational process, an N-terminal hydrophobic segment of the nascent polypeptide, called the "signal sequence," is recognized by a signal recognition particle and targeted to the endoplasmic reticulum membrane by an interaction between the signal recognition particle and a membrane receptor. The signal sequence enters the endoplasmic reticulum membrane and the following nascent polypeptide chain begins to pass through the translocation apparatus in the endoplasmic reticulum membrane. The signal sequence of a secreted protein or a type I membrane protein is cleaved by a signal peptidase on the luminal side of the endoplasmic reticulum membrane and is excised from the translocating chain. The rest of the secreted protein chain is released into the lumen of the endoplasmic reticulum. A type I membrane protein is anchored in the membrane by a second hydrophobic segment, which is usually referred to as a "transmembrane domain." The C-terminus of a type I membrane protein is located in the cytosol of the cell, while the N-terminus is displayed on the cell surface.

In contrast, certain proteins have a signal sequence that is not cleaved, a "signal anchor sequence," which serves as a transmembrane segment. A signal anchor type I protein has a C-terminus that is located in the cytosol, which is similar to type I membrane proteins, whereas a signal anchor type II protein has an N-terminus that is located in the cytosol.

Several insect cell systems have been devised to express a fusion protein comprising a foreign amino acid sequence and a transmembrane domain. In one system, an expression vector was designed to allow fusion of a heterologous protein to the amino-terminus of the *Autographa californica* nuclear polyhedrosis virus major envelop glycoprotein, gp64 (Mottershead et al., *Biochem. Biophys. Res. Commun.* 238:717 (1997)). Gp64, a type I integral membrane protein, functions as an anchor for the heterologous amino acid sequence, which is displayed on the surface of baculovirus particles (Monsma and Blissard, *J. Virol.* 69:2583 (1995)). More recently, Ernst et al., *Nucl. Acids Res.* 26:1718 (1998), described a baculovirus surface display system for the production of an epitope library. In this case, a nucleotide sequence encoding a particular epitope was inserted into an influenza virus hemagglutinin gene. Influenza virus hemagglutinin, like gp64, is a type I integral membrane protein, which provides a membrane anchor for the foreign amino acid sequence (see, for example, Lamb and Krug, "Orthomyxoviridae: The Viruses and Their Replication," in *Fundamental Virology*, 3$^{rd}$ Edition, pages 606–647 (Lippincott-Raven Publishers 1996)).

While both yeast and insect systems are useful for expressing eukaryotic polypeptides, post-translational modification of mammalian proteins in these systems does not necessarily produce proteins that are similar to those produced by mammalian cells. Accordingly, researchers are interested in developing display systems that use mammalian cells.

Cell surface display methods have been used to select molecules that encode proteins having a signal sequence or a transmembrane domain. For example, several techniques rely upon selection for nucleic acid fragments encoding a signal sequence to identify cDNA molecules that encode secreted proteins or type I membrane proteins (see, for example, Tashiro et al., Science 261:600 (1993); Yokoyama-Kobayashi et al., Gene 163:193 (1995)). According to these methods, a 5'-terminal fragment of the test cDNA is fused to a reporter gene, and the construct is introduced into cultured cells. If the fusion protein has a functional signal sequence, the product of the reporter gene will be detected in the cell membrane or in the culture medium. Similarly, Davis et al., Science 266:816 (1994), described an expression cloning method in which cDNA molecules encoding membrane-bound ligands were transfected into mammalian cells. Cells that expressed a membrane-bound ligand of interest were localized using detectably labeled soluble receptors, and cDNA encoding the ligand was rescued from the labeled cells.

In a related selection approach, Yokoyama-Kobayashi et al., Gene 228:161 (1999), described a method to test whether a hydrophobic sequence located near the N-terminus of a protein functions as a type II signal anchor. Here, a cDNA fragment containing the putative type II signal anchor of a target gene was fused to the 5'-end of a reporter gene. Transfected cells expressed the fusion protein on the cell surface.

Skarnes et al., Proc. Nat'l Acad. Sci. USA 92:6592 (1995), described a gene trap method that relies upon capturing the N-terminal signal sequence of an endogenous gene to generate an active β-galactosidase fusion protein, which is active in the cytosol, but not in the lumen of the endoplasmic reticulum (also see, Skarnes, U.S. Pat. No. 5,767,336). Briefly, a vector was designed that expressed a fusion protein containing a transmembrane domain of a type I membrane protein and β-galactosidase. The vector was introduced into cultured mammalian cells and allowed to integrate into the genome. Insertion of the vector into genes that contain a signal sequence produced a fusion protein that is inserted into the endoplasmic reticulum membrane in a type I configuration. The presence of the signal sequence results in an active β-galactosidase moiety that is located in the cytosol. In contrast, insertion of the vector into a gene that lacks a signal sequence results in a fusion protein that is inserted into the endoplasmic reticulum membrane in a type II orientation. Skarnes et al. suggested that, in the absence of a signal sequence, the transmembrane domain of the fusion protein acts a signal anchor sequence. Since the β-galactosidase moiety of the fusion protein is not located in the cytosol, β-galactosidase activity is lost. A modification of this approach requires an expression vector comprising a chimeric gene that contains a secretory lumen-sensitive indicator marker and a type II secretory protein transmembrane domain that is positioned N-terminally of the marker (Skarnes, U.S. Pat. No. 5,789,653).

Thus, the methods of Skarnes et al. rely upon the presence of a signal sequence in the target protein to correct a membrane orientation imposed by an exogenous transmembrane domain. A foreign transmembrane domain can also be used to force expression of proteins to the surface of mammalian cells. For example, Yang, U.S. Pat. No. 5,665,590, described a method for cloning genes or gene fragments that encode cell surface proteins or secreted proteins. In this approach, a cDNA library is cloned into expression vectors that encode an identifiable marker and a membrane anchoring segment. If a cloned cDNA molecule encodes a polypeptide having a signal sequence, then cells producing the encoded polypeptide should express the polypeptide and the identifiable marker as a cell surface protein attached by the membrane anchoring segment. This method requires the insertion of a cDNA molecule, which includes an intact 5'-end, upstream of nucleotide sequences encoding the identifiable marker and the membrane anchoring segment.

pDisplay™ is an example of a commercially available vector that is used to display a polypeptide on the surface of a mammalian cell (INVITROGEN Corp.; Carlsbad, Calif.). In this vector, a multiple cloning site resides between sequences that encode two identifiable peptides, hemagglutinin A and myc epitopes. The vector also includes sequences that encode an N-terminal signal peptide derived from a murine immunoglobulin κ-chain, and a type I transmembrane domain of platelet-derived growth factor receptor, located and the C-terminus. In this way, a protein of interest is expressed by a transfected cell as an extracellular fusion protein, anchored to the plasma membrane at the fusion protein C-terminus by the transmembrane domain.

Methods that rely upon the selection of certain features, such as a signal sequence or transmembrane domain, cannot be used to isolate genes encoding all types of proteins. Moreover, these methods require that the cloned gene or gene fragment includes an intact 5'-end that encodes the signal sequence. While more generally useful for displaying cloned genes, the pDisplay™ vector has a number of drawbacks. For example, the cloned gene will be expressed as an internal segment of a fusion protein, which means that both ends of the cloned gene must be inserted in-frame with the expression vector. Consequently, the vector is most suited for the display of a protein encoded by a known nucleotide sequence that can be engineered to produce the displayed fusion protein. In addition, the pDisplay™ vector is not well suited for the display of representative full-length libraries. This is so because the polypeptide encoded by the cDNA must be configured as an internal fusion protein, which means that the cloned cDNA must not contain the endogenous translation termination codon, located at the C-terminus of the gene. The pDisplay™ vector system, therefore, is best suited for cloning randomly primed cDNA molecules, which are shorter and are not representative of full-length cDNA libraries.

Accordingly, a need still exists for a simple method for expressing any polypeptide, and especially a full-length protein, in a cell surface display system.

BRIEF SUMMARY OF THE INVENTION

The present invention provides nucleic acid molecules and methods for expressing a peptide or polypeptide on the surface of a eukaryotic cell. These methods include strategies for producing a fusion protein that comprises a membrane anchor, which allows extracellular attachment of the fusion protein in a type II orientation.

DETAILED DESCRIPTION OF THE INVENTION

1. Overview

Figure 1:
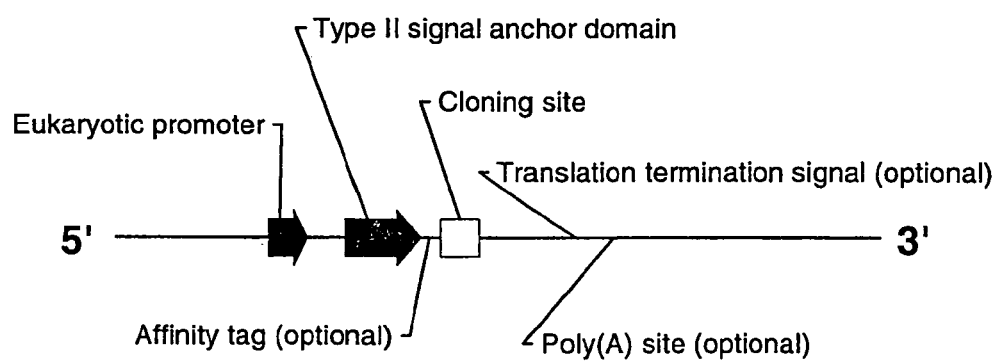
FIG. 1 shows a diagram of the basic components of one type of cell surface display vector, as described herein. A translation termination signal or polyadenylation signal sequence ("Poly(A) site") can be provided by the cloned gene or gene fragment.

The methods described herein provide a means to display a full-length and post-translationally processed protein encoded by an engineered nucleotide sequence, or to display a multiplicity of proteins encoded by cloned DNA molecules, such as an oligo dT-primed cDNA library, or a random-primed cDNA library. In brief, the display system uses the signal anchor domain sequences of type II cell surface proteins to anchor recombinant proteins onto the surface of transfected cells. As described above, a characteristic feature of type B cell surface proteins is that they are held within the cellular membrane by a single hydrophobic transmembrane domain and are oriented with their carboxyl terminus outside the cell. This orientation is opposite to a type I cell surface protein, in which the N-terminus is displayed outside the cells.

One advantage of a display system that uses a type II signal anchor domain for cell surface attachment is that the recombinant protein can be produced as fusion protein having only one fusion junction. This means that one in three cDNA molecules will produce an in-frame fusion gene when oligo-dT primed cDNA molecules are cloned directionally into an expression vector of the present invention. In contrast, only one in nine randomly-primed cDNA molecules would produce an in-frame fusion protein when the cDNA sequence must be inserted between nucleotide sequences that encode a signal sequence and a type I transmembrane domain. In addition, certain embodiments of the present invention allow the expression of polypeptides from a gene library regardless of whether or not the genes include in-frame endogenous translation termination codons. This feature allows the display of full-length proteins encoded by oligo dT-primed cDNA molecules.

Although it is possible to take advantage of histological examination of fixed transfected cells that express a fusion protein, the presently described methods provide the option of examining cloned functional proteins on the surface of living cells. The use of live cells not only avoids the risk of protein denaturation associated with fixation techniques, but also enables the identification of cells expressing desired proteins by cell sorting and similar methods.

As described herein, the present invention provides isolated nucleic acid molecules, comprising, or consisting of, (a) a eukaryotic promoter, (b) a nucleotide sequence encoding a type II signal anchor domain segment, and (c) a cloning site, wherein the isolated nucleic acid molecule comprises elements (a) to (c) in a 5' to 3' order. Illustrative promoters include cytomegalovirus promoter, rous sarcoma virus promoter, human immunodeficiency virus long tenninal repeat promoter, simian virus 40 promoter, and herpes simplex virus thymidine kinase promoter. The cloning site of the nucleic acid molecule can be a multiple cloning site.

In addition, isolated nucleic acid molecules can further comprise a nucleotide sequence that encodes a spacer peptide, wherein the spacer peptide-encoding nucleotide sequence resides between the type II signal anchor domain-encoding nucleotide sequence and the cloning site, and wherein the spacer peptide comprises at least ten amino acids. Alternatively, isolated nucleic acid molecules can comprise a nucleotide sequence that encodes an affinity tag, wherein the affinity tag-encoding nucleotide sequence resides between the type II signal anchor domain-encoding nucleotide sequence and the cloning site. Moreover, nucleic acid molecules can comprise both a spacer peptide-encoding nucleotide sequence and an affinity tag-encoding nucleotide sequence.

The present invention also contemplates nucleic acid molecules comprising at least one of a splice junction and an intron, wherein the intron-encoding nucleotide sequence resides between the promoter and the type II signal anchor domain-encoding nucleotide sequence.

Nucleic acid molecules can further comprise at least one sequence, two, or three sequences selected from the group consisting of (a) a translation termination sequence, (b) a polyadenylation signal sequence, and (c) a transcription termination sequence. A nucleic acid molecule that comprises at least two of sequences (a)–(c) includes the sequences in the following 5' to 3' order: translation termination sequence, polyadenylation signal sequence, and transcription termination sequence.

The present invention further provides isolated nucleic acid molecules, wherein at least one nucleotide is added or subtracted to the cloning site to facilitate the expression of gene fragments in multiple reading frames.

The present invention also contemplates isolated nucleic acid molecules, comprising (a) a eukaryotic promoter, (b) a nucleotide sequence encoding a type II signal anchor domain, and (c) a gene or gene fragment, wherein the isolated nucleic acid molecule comprises elements (a) to (c) in a 5' to 3' order, and wherein the gene or gene fragment resides in-frame with the nucleotide sequence that encodes the type II signal anchor domain.

Such nucleic acid molecules can further comprise at least one of a translation termination sequence, which resides in a 3' position relative to the gene or gene fragment, a polyadenylation signal sequence, wherein the polyadenylation signal sequence is located 3' to the translation termination sequence, and a transcription termination sequence, wherein the transcription termination sequence resides in a 3' position relative to the polyadenylation signal sequence. These translation termination sequences, polyadenylation signal sequences, and transcription termination sequences can reside within the gene or gene fragment. Isolated nucleic acid molecules of the present invention can comprise a type II signal anchor domain-encoding nucleotide sequence, which is heterologous with respect to the gene or gene fragment.

The present invention also contemplates vectors and expression vectors comprising such nucleic acid molecules. These vectors can further comprise at least one selectable marker gene, and can further comprise at least two origins of replication, wherein one origin of replication facilitates replication in an expression cell type, and wherein a second origin of replication facilitates replication in an amplification cell type, and wherein the expression cell type is eukaryotic and the amplification cell type is prokaryotic.

The present invention includes recombinant host cells comprising such vectors and expression vectors. Illustrative host cells include prokaryotic host cells, and eukaryotic host cells. Exemplary eukaryotic host cells include mammalian, avian, fungal, and insect cells.

The present invention also contemplates methods for selecting nucleic acid molecules encoding polypeptides, comprising: (a) transfecting an expression vector of the present invention into a eukaryotic host cell to produce a recombinant host cell, (b) incubating the recombinant host cell under conditions and a time sufficient for expression of the gene or gene fragment, and (c) selecting recombinant host cells that comprise the polypeptide product of the gene or gene fragment on the cell surface.

The present invention also provides methods for selecting nucleic acid molecules encoding polypeptides, comprising: (a) incubating recombinant host cells, which comprise an expression vector of the present invention, under conditions and a time sufficient for expression of the gene or gene fragment, and (b) selecting recombinant host cells that comprise the polypeptide product of the gene or gene fragment on the cell surface.

The present invention also contemplates methods for selecting nucleic acid molecules encoding polypeptides, comprising: (a) obtaining a collection of genes or gene fragments, (b) cloning the gene or gene fragments into the cloning site of a vector or expression vector of the present invention, (c) transfecting the product of step (b) into a eukaryotic cell, (d) incubating the transfected cells under conditions and a time sufficient for expression of the gene or gene fragment, and (e) selecting transfected cells that that comprise the polypeptide product of the gene or gene fragment on the cell surface.

Other methods for selecting nucleic acid molecules encoding polypeptides, comprise: (a) cloning a collection of genes or gene fragments into the cloning site of a vector or expression vector of the present invention, (b) incubating recombinant eukaryotic cells that comprise the product of step (a) under conditions and a time sufficient for expression of the gene or gene fragment, and (c) selecting recombinant cells that that comprise the polypeptide product of the gene or gene fragment on the cell surface.

In addition, the present invention provides methods for selecting a member of a complementary/anti-complementary binding pair, comprising: (a) cloning a plurality of genes or gene fragments into the cloning site of a vector or expression vector of the present invention, wherein the plurality of genes or gene fragments includes a gene or gene fragment that encodes the first member of a complementary/anti-complementary binding pair (b) transfecting the product of step (a) into eukaryotic cells, (c) incubating the transfected cells under conditions and a time sufficient for expression of the gene or gene fragment, and (d) selecting transfected cells. that that comprise the polypeptide product of the gene or gene fragment on the cell surface by exposing the transfected cells to the second member of the complementary/anti-complementary binding pair.

In a variation of this approach, a method for isolating a member of a complementary/anti-complementary binding pair, comprises: (a) incubating recombinant eukaryotic cells that comprise an expression vector of the present invention, under conditions and a time sufficient for expression of a gene or gene fragment, wherein the gene or gene fragment encodes the first member of a complementary/anti-complementary binding pair and (b) selecting recombinant cells that that comprise the polypeptide product of the gene or gene fragment on the cell surface by exposing the recombinant cells to the second member of the complementary/anti-complementary binding pair.

Examples of complementary/anti-complementary binding pairs include a receptor/ligand pair or an antibody/epitope pair. In certain variations of such methods, the second member of the complementary/anti-complementary binding pair can mobilized on a solid support. Moreover, the second member of the complementary/anti-complementary binding pair can be detectably labeled.

Particular methods of the present invention utilize vectors comprising a gene or gene fragment that comprises genomic DNA or cDNA. Such cDNA can be synthesized from a primer comprising a poly(dT) sequence or synthesized from at least one primer comprising a sequence of random nucleotides.

The present invention also provides kits comprising a nucleic acid molecule, vector, expression vector, or recombinant host cell, as described herein.

These and other aspects of the invention will become evident upon reference to the detailed description and attached drawings. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., $\alpha$-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule. For example, representative contigs to the polynucleotide sequence 5' ATGGAGCTT 3' are 5' AGCTTgagt 3' and 3' tcgacTACC 5'.

The term "structural gene" refers to a nucleic acid molecule that is transcribed into messenger RNA (mRNA), which is then translated into a sequence of amino acids characteristic of a specific polypeptide. A "gene of interest" can be a structural gene.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (McGehee et al., *Mol. Endocrinol.* 7:551 (1993)), cyclic AMP response elements, serum response elements (Treisman, *Seminars in Cancer Biol.* 1:47 (1990)), glucocorticoid response elements, and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA. For example, a DNA molecule containing a non-host DNA segment that encodes a polypeptide operably linked to a host DNA segment comprising a transcription promoter is considered to be a heterologous DNA molecule. Conversely, a heterologous DNA molecule can comprise an endogenous gene operably linked with a promoter derived from a non-host gene. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide synthesized within a cell from a heterologous nucleic acid molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "type II signal anchor domain," or "type II transmembrane domain," refers to a hydrophobic amino acid sequence found in eukaryotic type n integral membrane proteins that, during translation, targets and anchors a polypeptide in the endoplasmic reticulum membrane with a type II orientation. The phrase "type II orientation," refers to a protein topology in which the N-terminus resides in the cytoplasm, while the C-terminus resides within the lumen of the endoplasmic reticulum or on an extracellular cell surface.

A "fusion protein" is a hybrid protein expressed by a nucleic acid molecule comprising nucleotide sequences of at least two genes. In this way, a fusion protein comprises as least two amino acid sequences that are not associated with each other in nature. As an illustration, Example Two describes a vector that expressed a fusion protein comprising a tumor necrosis factor-α: transmembrane domain and a thrombopoietin moiety.

When used to describe a component of an expression vector, the language "gene or gene fragment" refers to a nucleotide sequence that encodes a polypeptide or peptide. The gene or gene fragment can be obtained from genomic DNA, from cDNA, or by an in vitro synthesis technique (e.g., polymerase chain reaction, chemical synthesis, and the like).

According to the methods described herein, a nucleic acid molecule may comprise a nucleotide sequence encoding a type II signal anchor domain and a gene (or gene fragment). If the type II signal anchor domain-encoding sequence and the gene (or gene fragment) are derived from different genes, then the type II signal anchor domain-encoding sequence is considered to be a heterologous type II signal anchor domain-encoding sequence, with respect to the gene (or gene fragment). An amino acid sequence produced from such a nucleic acid molecule comprises a type II signal anchor domain that is heterologous with respect to the polypeptide or peptide encoded by the gene or gene fragment.

Figure 2:
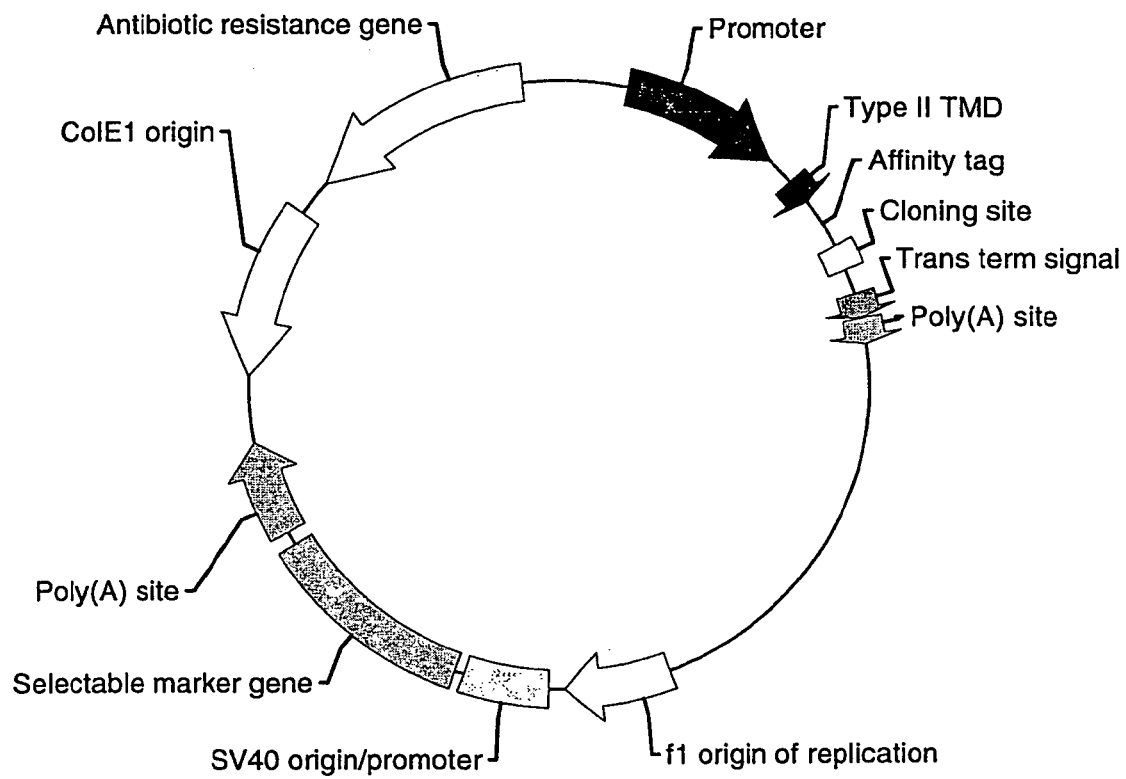
FIG. 2 shows a diagram of an illustrative cell surface display expression vector. Poly(A) site: polyadenylation signal sequence; TMD: transmembrane domain; Trans term signal: translation termination signal.
Figure 3:
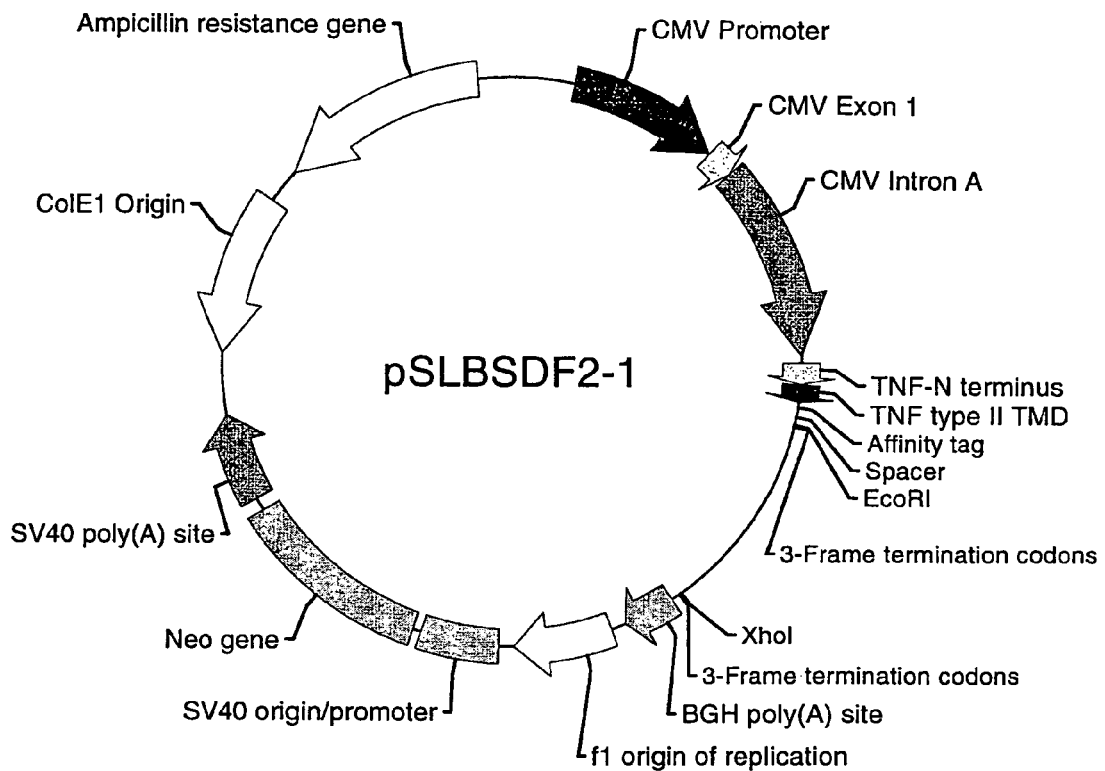
FIG. 3 shows a diagram of vector pSLBSDF2-1, which was used to express thrombopoietin and *Arabidoposis thaliana* peroxidase, as described in the examples. BGH: bovine growth hormone; CMV: cytomegalovirus; Poly(A) site: polyadenylation signal sequence; TMD: transmembrane domain; TNF: tumor necrosis factor; Trans term signal: translation termination signal.

Conveniently, an expression vector can be constructed that comprises a nucleotide sequence encoding a type II signal anchor domain. FIGS. 2 and 3 provide examples of such vectors. The isolated type II signal anchor domain is referred to as a "type II signal anchor domain segment." The amino acid sequence of a type II signal anchor domain segment can be derived from a naturally occurring polypeptide (e.g., tumor necrosis factor, as illustrated in FIGS. 2 and 3), or the amino acid sequence can be devised following the guidelines discussed below.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins, colony stimulating factors, interferons, stem cell growth factors, erythropoietin, and thrombopoietin.

The phrase "complement/anti-complement pair" denotes non-identical moieties that form a non-covalently associated, stable pair under appropriate conditions. For instance, biotin and avidin (or streptaviding are prototypical members of a complement/anti-complement pair. Other exemplary complement/anti-complement pairs include receptor/ligand pairs, antibody/antigen (or hapten or epitope) pairs, sense/antisense polynucleotide pairs, and the like.

An "antibody fragment" is a portion of an antibody such as F(ab')$_2$, F(ab)$_2$, Fab', Fab, and the like. Regardless of structure, an antibody fragment binds with the same antigen that is recognized by the intact antibody.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "detectable label" is a molecule or atom which can be conjugated to a polypeptide to produce a molecule useful for identifying cells that express the binding partner of the polypeptide. Examples of detectable labels include chelators, photoactive agents, radioisotopes, fluorescent agents, paramagnetic ions, or other marker moieties.

Due to the imprecision of standard analytical methods, molecular weights and lengths of polymers are understood to be approximate values. When such a value is expressed as "about" X or "approximately" X, the stated value of X will be understood to be accurate to ±10%.

3. Design of Expression Vectors

Expression vectors that are suitable for production of a protein in eukaryotic cells typically contain (1) prokaryotic DNA elements coding for a bacterial replication origin and an antibiotic resistance marker to provide for the growth and selection of the expression vector in a bacterial host, (2) eukaryotic DNA elements that control initiation of transcription, such as a promoter, and (3) DNA elements that control the processing of transcripts, such as a transcription termination/polyadenylation signal sequence.

An expression vector of the present invention comprises, in a 5' to 3' direction, a eukaryotic promoter, a signal anchor domain of a type II protein, and a nucleotide sequence that is a cloning site, which allows insertion of a gene or gene fragment. In addition, the expression vector can also include translation termination, polyadenylation signal, and transcription termination sequences, although, such elements may be provided by the polypeptide-encoding gene or gene fragment. The expression vector can also include a nucleotide sequence that encodes an affinity tag. An affinity tag-encoding sequence can be positioned, for example, between the type II signal anchor domain-encoding sequence and the cloning site. The expression vector can also contain a nucleotide sequence that encodes a spacer peptide, which can also be located between the type II signal anchor domain-encoding sequence and the cloning site. Studies have shown that the presence of an intron can increase the efficiency of recombinant protein expression. Accordingly, an expression vector of the present invention can include an intron sequence located, for example, between the promoter and the type II signal anchor domain-encoding sequence. Expression vectors can also contain additional elements such as a gene that encodes a selectable marker, an antibiotic resistance gene for selection in a bacterial host, an SV40 early promoter and origin, which drives expression of the selectable marker gene and allows episomal replication in cells containing SV40 large T antigen, a ColE1 origin, which provides replication and growth in *E. coli*, and the like.

The expression vectors described herein can be used for a variety of applications. For example, antigen display on the surface of cells can be used to modulate immune functions (see, for example, Cho et al., *J. Immunol. Meth.* 220:179 (1998)). The display of an otherwise secreted protein or non-secreted protein on the cell surface is also useful for studying the interaction between a complement/anti-complement pair. As an illustration, the examination of the interaction between a receptor-ligand pair provides an approach to rational drug design. The expression vectors can be used to clone unknown members of a complement/anti-complement pair. For example, a labeled probe consisting of a known member of a receptor-ligand pair can be used to screen cells transfected with a cell surface display cDNA library. The positive cell can be identified by direct binding of the probe to its partner expressed on the cell surface. The cDNA encoding the unknown partner can then be recovered from the recombinant host cells. Alternatively, the labeled probe can be used as a cell sorting reagent to enrich for a population of library transfected cells expressing an interacting partner to the probe.

In addition, various bioactive proteins can be displayed on the cell surface to produce a cell with new useful functions or properties. Bioactive reactive molecules include chemoattractants, adhesion molecules, antigens, antibodies, enzymes, growth factors, receptors, and the like. The expression of exogenous proteins on the cell surface can also be used as a live recombinant vaccine.

The display of polypeptides on the surface of a recombinant cells can be used to deliver bioactive molecules to other cells. This mode of delivery has the advantage that the activity is confined to the cell surface, resulting in an activity that is exerted locally and specific only to nearby cells. Since the fusion protein products are not secreted, the specific activity of the fusion protein is not reduced by dilution of the medium.

The cell surface display system can be used to characterize and identify polypeptides, or peptides, that mediate cell differentiation and growth. For example, cDNA molecules encoding test polypeptides can be displayed on the surface of mammalian cells, which are co-cultured with embryonic stem cells. Under co-culture conditions, the recipient cells displaying the test polypeptides are incorporated into embryoid bodies formed by the stem cells. Active polypeptides are identified by the ability of the recipient cells to induce growth and differentiation of embryoid body cells. As another illustration, the display system described herein can produce a collection of recipient cells, each of which displays a polypeptide encoded by a cDNA from a cDNA library. When co-cultured with stem cells, cDNA molecules encoding active polypeptides can be identified. cDNA molecules encoding active polypeptides that affect growth or differentiation can also be identified by displaying polypeptides encoded by complex cDNA libraries directly on the surface of stem cells.

A. Expression Vector Components

To express a gene, a nucleic acid molecule encoding the protein must be operably linked to regulatory sequences that control transcriptional expression and then, introduced into a host cell. In addition to transcriptional regulatory sequences, such as promoters and enhancers, expression vectors can include transcriptional and translational regulatory sequences. As an illustration, the transcriptional and translational regulatory signals suitable for a mammalian host may be derived from viral sources, such as adenovirus, bovine papilloma virus, simian virus, or the like, in which the regulatory signals are associated with a particular gene that has a high level of expression. Suitable transcriptional and translational regulatory sequences also can be obtained from mammalian genes, such as actin, collagen, myosin, and metallothionein genes.

Suitable transcriptional regulatory sequences include a promoter region sufficient to direct the initiation of RNA synthesis. Illustrative eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)); the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control expression of the gene of interest in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

The signal anchor domain component of an expression vector of the present invention can be any type II signal anchor domain sequence, which is capable of providing attachment to the cell surface in a type II orientation. Examples of type II cell surface proteins that comprise such signal anchor domains include influenza neuraminidase, the small hydrophobic proteins of the paramyxovirus simian virus, the paramyxovirus hemagglutinin-neuraminidase, human and rat asialoglycoprotein receptors, chicken hepatic lectin, human and rabbit neutral endopeptidase, human intestinal aminopeptidase, rabbit sucrase-isomaltase receptor, human transferrin receptor, hepatic glycoprotein receptor, human IgE receptor, murine 1,4-β-galactosyltransferase, human P-glycoprotein receptor, human invariant chains of class II histocompatibility antigens, rat sodium channel proteins, rat brain, muscle and liver glucose transporter proteins, bacterial leader peptidase, and members of the tumor necrosis factor/nerve growth factor superfamily (see, for example, Wolfe et al., *J. Biol. Chem.* 258:12073 (1983); Chiacchi and Drickamer, *J. Biol. Chem.* 259:15440 (1984); Hiebert et al., *J. Virol.* 54:1 (1985); Hiebert et al., *J. Virol.* 55:744 (1985); Schneider et al., *Nature* 311:675 (1984); Spiess and Lodish, *Proc. Nat'l Acad. Sci. USA* 82:6465 (1985); Strubin et al., *EMBO J.* 3:869 (1984); Semenza, *Annu. Rev. Cell Biol.* 2:255 (1986); Lipp and Dobberstein, *J. Cell Biol.* 106:1813 (1988); Hartmann et al., *Proc. Nat'l Acad. Sci. USA* 86:5786 (1989)). Moreover, Chou and Elrod, *Proteins: Structure, Function, and Genetics* 34:137 (1999), disclose 152 type II membrane proteins, which they used to devise a method for predicting whether an amino acid sequence confers the type II membrane protein structure.

The illustrative pSLBSDF2-1 vector contains a nucleotide sequence that encodes the type II signal anchor domain of human tumor necrosis factor-α (see FIG. 3). Tumor necrosis factor-α (TNF-α) exists as a type II membrane bound precursor which is cleaved and released by a converting enzyme, and its signal anchor domain sequence is well defined (Utsumi et al., *J. Biol. Chem.* 268:9511 (1993); Utsumi et al., *Molec. Cell. Biol.* 15:6398 (1995); Tang et al., *Biochem.* 35:8226, (1996); Moss et al., *Nature* 385:733 (1997); Rosendahl et al., *J. Biol. Chem.* 272:24588 (1997)). The converting enzyme cleavage site is also well defined (see, for example, Tang et al., *Biochem.* 35:8226 (1996)).

The type II signal anchor domain in pSLBSDF2-1 lacks a cleavage site to prevent the release of displayed protein from the cell surface. The illustrative pSLBSDF2-1 vector includes a TNF-α transmembrane domain (signal anchor domain) with the following amino acid sequence: LFLSL FSFLI VAGAT TLFCL LHFGV I (SEQ ID NO:2). Preferably, the vector also includes a TNF-α N-terminus sequence (MSTES MIRDV ELAEE ALPKK TGGPQ GSRRC; SEQ ID NO:3) positioned at the N-terminal end of the transmembrane domain.

A nucleic acid molecule that encodes a synthetic sequence with functional properties of a type II signal anchor domain can also be used for the expression vectors of the present invention. A synthetic type II signal anchor domain sequence can be constructed based on the known functional requirements (see, for example, Parks and Lamb, *Cell* 64:777 (1991)). Studies indicate that the balance between the length of the hydrophobic segment and N-terminal charge is important for the orientation of cell surface proteins. For example, Sakaguchi et al., *Proc. Nat'l Acad. Sci. USA* 89:16 (1992), found that hydrophobic segments consisting of 7–10 leucine residues function as type II signal sequences, whereas segments with 12–15 leucine residues showed different topogenic functions, behaving as a signal sequence or type II signal anchor domain sequence depending on the net charge on the N-terminal. In the type II surface proteins, about 90% have a net positive cytoplasmic charge in the 15-residue transmembrane-flanking region of the non-translocated amino terminus (Hartmann et al., *Proc. Nat'l Acad. Sci. USA* 86:5786 (1989)). Lipp and Dobberstein, *J. Cell Biol.* 106:1813 (1988), indicate that a type II signal anchor domain has three distinct segments: (1) a net positively-charged N-terminal region, (2) a central segment of hydrophobic amino acid residues, containing at least 16 amino acid residues, and (3) a hydrophilic C-terminal portion.

Alternatively, a signal sequence may be modified to be functionally equivalent to a type II or a type I signal anchor domain for use in the expression vectors described herein. Modifications include: (a) an increase in the length of the hydrophobic segment to enhance membrane anchorage, (b) increasing or decreasing net charge to control orientation within the membrane, and (c) the removal of cleavage site for a signal peptidase (see, for example, Chou and Kendall, *J. Biol. Chem.* 265:2873 (1990); Nilsson et al., *J. Cell Biol.* 126:1127 (1994); Parks, *J. Biol. Chem.* 271:7187 (1996)).

The inclusion of an affinity tag is useful for the identification or selection of cells displaying the fusion protein. Examples of affinity tags include polyHistidine tags (which have an affinity for nickel-chelating resin), c-myc tags (e.g., EQKLI SEEDL; SEQ ID NO:4) which are detected with anti-myc antibodies, calmodulin binding protein (isolated with calmodulin affinity chromatography), substance P, the RYIRS tag (which binds with anti-RYIRS antibodies), a hemagglutinin A epitope tag (e.g., YPYDV PDYA; SEQ ID NO:5) which is detected with an antibody, the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The cloning site can be a multicloning site. Any multicloning site can be used, and many are commercially available. Particularly useful multicloning sites allow the cloning of a gene or gene fragment in all three reading frames.

The expression vector can also include a transcription termination sequence, and optionally, a polyadenylation signal sequence. For example, pSLBSDF2-1 includes a bovine growth hormone polyadenylation signal sequence and transcription termination sequence to enhance mRNA stability. An expression vector need not contain transcription termination and polyadenylation signal sequences, because these elements can be provided by the cloned gene or gene fragment.

As shown in FIG. 3, pSLBSDF2-1 includes two sets of three-frame termination codons, one set located 3' to an EcoRI site, and one set located 5' to a XhoI site. The first set of termination codons can be used for cDNA molecules cloned into the EcoRI site. The second set of termination codons can be used for cDNA molecules that are cloned directionally as EcoRI-XhoI fragments. Such DNA molecules can be produced, for example, by random priming.

The expression vector can include a nucleotide sequence that encodes a selectable marker. A wide variety of selectable marker genes are available (see, for example, Kaufman, *Meth. Enzymol.* 185:487 (1990); Kaufman, *Meth. Enzymol.* 185:537 (1990)). For example, one suitable selectable marker is a gene that provides resistance to the antibiotic neomycin. In this case, selection is carried out in the presence of a neomycin-type drug, such as G-418 or the like. Bleomycin-resistance genes, such as the Sh ble gene, are also useful selectable marker genes for the presently described methods. These genes produce a protein that inhibits the activity of bleomycin/phleomycin-type drugs, such as ZEOCIN (Gatignol et al., *Mol. Gen. Genet.* 207:342 (1987); Drocourt et al., *Nucl. Acids Res.* 18:4009 (1990)). ZEOCIN is toxic in a broad range of cell types, including bacteria, fungi, plant, avian, insect, and mammalian cells. Additional selectable markers include hygromycin B-phosphotransferase, the AUR1 gene product, adenosine deaminase, aminoglycoside phosphotransferase, dihydrofolate reductase, thymidine kinase, and xanthine-guanine phosphoribosyltransferase (see, for example, Srivastava and Schlessinger, *Gene* 103:53 (1991); Romanos et al., "Expression of Cloned Genes in Yeast," in *DNA Cloning 2: Expression Systems*, 2nd Edition, pages 123–167 (IRL Press 1995); Markie, *Methods Mol. Biol.* 54:359 (1996); Pfeifer et al., *Gene* 188:183 (1997); Tucker and Burke, *Gene* 199:25 (1997); Hashida-Okado et al., *FEBS Letters* 425:117 (1998)). Selectable marker genes can be cloned or synthesized using published nucleotide sequences, or marker genes can be obtained commercially.

A expression vector can also include an SV40 origin. This element can be used for episomal replication and rescue in cell lines expressing SV40 large T antigen.

The expression vectors of the present invention can express any nucleic acid molecule encoding an amino acid sequence of interest as a fusion protein comprising a type II signal anchor domain. Typically, the type II signal anchor domain and the amino acid sequence of interest are not associated with each other in nature, and therefore, are heterologous with respect to each other. That is, these two amino acid sequences typically are encoded by nucleotide sequences of different naturally-occurring genes.

Exemplary amino acid sequences of interest include full-length polypeptides, and fragments of full-length polypeptides. Although the cloned gene or gene fragment can encode a peptide, the gene or gene fragment preferably encodes a polypeptide comprising more than 10 amino acids. For example, such polypeptides can consist of about 10 to about 20 amino acids, about 20 to about 40 amino acids, about 40 to about 100 amino acids, or greater than 100 amino acids.

A gene or gene fragment suitable for insertion into an expression vector can be obtained from cDNA, which is prepared by any method known in the art. For example, cDNA molecules can be synthesized by random priming. Moreover, such primers can be linked to restriction endonuclease sites found in the vector. Alternatively, cDNA molecules can be prepared by oligo d(T) priming. A gene or gene fragment can also be obtained from genomic DNA or by chemical synthesis. Standard methods for preparing suitable genes or gene fragments are known to those in the art (see, for example, Ausubel et al. (eds.), *Short Protocols in Molecular Biology*, 3rd Edition (John Wiley & Sons 1995) ["Ausubel 1995"]).

After constructing the expression vector, the vector can be propagated in a host cell to synthesize nucleic acid molecules for the generation of a nucleic acid polymer. Vectors, often referred to as "shuttle vectors," are capable of replicating in at least two unrelated expression systems. To facilitate such replication, the vector should include at least two origins of replication, one effective in each replication system. Typically, shuttle vectors are capable of replicating in a eukaryotic system and a prokaryotic system. This enables detection of protein expression in eukaryotic hosts, the "expression cell type," and the amplification of the vector in the prokaryotic hosts, the "amplification cell type." As an illustration, one origin of replication can be derived from SV40, while another origin of replication can be derived from pBR322. Those of skill in the art know of numerous suitable origins of replication.

Vector propagation is conveniently carried out in a prokaryotic host cell, such as *E. coli* or *Bacillus subtilus*. Suitable strains of *E. coli* include BL21(DE3), BL21(DE3) pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel 1995; Wu et al., *Methods in Gene Biotechnology* (CRC Press, Inc. 1997)).

B. Expression Vector Variations

Expression vectors can be designed to comprise two "transcriptional units," in which a transcriptional unit comprises a transcriptional regulatory element, a coding region, and a transcription terminator. One coding region would encode the polypeptide of interest, while the second coding region would encode the selectable marker. Both transcriptional units may contain the same transcriptional regulatory element.

As an illustration, Examples 1 and 2 describe studies with an expression vector, designated as "pSLBSDF2-1," which includes two transcriptional units. One transcriptional unit comprises a cytomegalovirus (CMV) promoter and intron which are operably linked with a nucleotide sequence encoding a tumor necrosis factor-α signal anchor domain, a nucleotide sequence that encodes an affinity tag, a nucleotide sequence that encodes a 13 amino acid residue spacer consisting of glycine and alanine residues to provide spatial freedom to the displayed protein, a cloning site, and termination and polyadenylation signal sequences. In the illustrative vector, the spacer has the following amino acid sequence: GGGGA AGGGG GAA (SEQ ID NO:1). A second transcriptional unit comprises an SV40 origin and promoter operably linked to a neomycin resistance gene. The pSLBSDF2-1 vector also includes an ampicillin resistance gene and a ColE1 origin for selection and propagation in *E. coli.*

A spacer offers the advantages of providing flexibility, and minimal steric interference with the folding or function of other portions of the fusion protein. Those of skill in the art can devise suitable spacers, which meet the requirement of an inert, flexible amino acid sequence. For example, a proline residue can be added to the illustrative spacer (SEQ ID NO:1) at the beginning, at the end, or at both the beginning and the end of the spacer. In the latter case, the proline residue would serve to isolate the spacer as a separate functional domain from the other parts of the protein. Such proline residues need not occur at the precise endpoints of the spacer. For example, proline residues can be inserted between one to four amino acid residues from the spacer endpoints. Moreover, spacers can be devised that include any of glycine, serine, and alanine residues, and that include from 10 to 30 or more amino acid residues. For example, suitable spacers can consist of 25 amino acid residues to provide spatial freedom to the displayed protein.

Alternatively, an expression vector can comprise two coding regions, which reside between a transcriptional regulatory element and a transcription terminator. In this case, each of the coding regions of the dicistronic message vector should have its own ribosome binding site (see, for example, Lee et al., *Nucl. Acids Res.* 12:6797 (1984)). For example, the second coding sequence of a dicistronic vector can encode a reporter protein used to identify a transfected cell that expresses the foreign genes. Illustrative reporter proteins include cell surface proteins that can be bound with antibodies to isolate cells with a fluorescent activated cell sorter, or other method. Another example of a reporter protein is an enzyme that catalyzes the formation of a detectable product from a suitable substrate. Moreover, the reporter protein itself may be detectable using its inherent physical properties, such as fluorescence or light emission.

Another approach accounts for gene or gene fragments that encode a polypeptide comprising a signal sequence. Proteins that span the cell membrane more than once, the so-called "multipass transmembrane proteins," comprise transmembrane segments having orientations determined by the most N-terminal transmembrane domain (see, for example, Hartmann et al., *Proc. Nat'l Acad. Sci. USA* 86:5786 (1989); Sato et al., *J. Biol. Chem.* 273:25203 (1998)). Transmembrane domains that follow this first domain alternate in orientation as the polypeptide spans the membrane. Multipass transmembrane proteins are illustrated by the seven-transmembrane domain G-protein coupled receptors. Fusion proteins with a type II transmembrane domain at its N-terminus, followed by an even number of transmembrane domains or a functionally equivalent hydrophobic amino acid sequence (e.g., a signal sequence) would display the remaining portion of the protein outside the cell. A vector, designated as "pSLSD-2," was designed to display protein containing an endogenous signal peptide sequence. pSLSD-2 is constructed by the insertion of a nucleotide sequence encoding a transmembrane domain upstream (5'-ward) of the cloning site of pSLBSDF2-1 to orient the protein with an endogenous signal sequence outside the cell.

4. Production of Recombinant Protein by Host Cells

The expression vector can be introduced into any eukaryotic cell, such as a mammalian cell, insect cell, avian cell, fungal cell, and the like. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

The baculovirus system provides an efficient means to introduce cloned genes of interest into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the gene or gene fragment into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). These vectors can be modified following the above discussion The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), *Sf*21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2-5\times10^5$ cells to a density of $1-2\times10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols,* Murray (ed.), pages 147–168 (The Humana Press, Inc. 1991), by Patel et al., "The baculovirus expression system," in *DNA Cloning 2: Expression Systems, 2nd Edition,* Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice,* Cleland et al. (eds.), pages 183–218 (John Wiley & Sons, Inc. 1996).

The expression vectors described herein can also be used to transfect fungal cells, including yeast cells. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors readily available and can be modified following the above discussion. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Laambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., Yeast 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

An expression vector can be introduced into host cells using a variety of standard techniques including calcium phosphate transfection, liposome-mediated transfection, microprojectile-mediated delivery, electroporation, and the like.

Standard methods for introducing expression vectors into mammalian, yeast, and insect cells are provided, for example, by Ausubel (1995). General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), page 163 (Wiley-Liss, Inc. 1996). Established methods for isolating recombinant proteins from a baculovirus system are described by Richardson (ed.), *Baculovirus Expression Protocols* (The Humana Press, Inc. 1995).

Expression vectors can be isolated from cells that produce a polypeptide of interest. If desired, expression vectors can be subjected to another round of selection based on expression of the identifiable polypeptide or, transfected into the amplification cell type. The transfected amplification cell type is then selected by the selectable marker, the vectors are purified and the nucleotide sequence of the gene or gene fragment is sequenced by any method known in the art. If the nucleotide sequence encodes only a portion of a complete polypeptide, then the nucleotide sequence can be used as a probe by methods known in the art to retrieve the entire gene.

5. Identification of Recombinant Host Cells that Express Fusion Protein and Recovery of Nucleic Acid Molecules Encoding the Fusion Protein There are various approaches to identifying recombinant host cells that express a polypeptide of interest on the extracellular surface. For example, the recombinant host cells can be cultured for a time sufficient to express the fusion protein on the cell surface. These cells are then combined with a reagent that specifically binds to the fusion protein, and that is labeled with a detectable tag. Suitable reagents in this regard include antibodies, ligands, soluble receptors and the like. Detectable tags suitable for use include fluorescent, fluorescence quenching, dye and magnetic tags and the like. In addition, any tag that modifies the light scattering properties of the target to which it is bound is suitable for use herein. The recombinant host cells are then sorted according to the presence or absence of detectable tag/reagent bound at the cell surface. Thus, in one step, recombinant host cells expressing a fusion protein are readily segregated from those in which a functional signal sequence is lacking. In one preferred embodiment, an automated machine that permits single cell examination (e.g., a flow cytometer) is used to detect and to select recombinant host cells that express a fusion protein at the cell surface. As an illustration, a fluorescence-activated flow cytometer is used to segregate cells that express a fusion protein.

The detectably labeled reagent can be used in either soluble form or bound to a solid support. The phrase "solid support" refers to any material capable of binding a member of a complementary/anti-complementary binding pair. Well-known solid supports include glass, polystyrene, polypropylene, polyethylene, dextran, nylon, amylases, natural and modified celluloses, polyacrylamides, agaroses, and magnetite. The solid support can have virtually any possible structural configuration so long as the bound reagent molecule is capable of binding with a fusion protein. Thus, the support configuration may be spherical, as in a bead (e.g., a magnetic bead), or cylindrical, as in the inside surface of a test tube, or the external surface of a rod. Alternatively, the surface may be flat, such as a sheet, a test strip, and the like. Those skilled in the art are aware of many other suitable solid supports.

Following identification or selection, the type II signal anchor domain nucleotide sequence can be used as a probe or as a PCR primer to recover sufficient amounts of the DNA of interest for sequencing. As an alternative, selected recombinant host cells can be cloned and expanded before DNA recovery with a probe or PCR primer. After the mixture of DNA molecules of interest is amplified, in one alternative, the recovered DNA can be recloned into the expression vector for additional cycles of enrichment. After enrichment, individual DNA clones can be isolated for sequencing. In another alternative, the mixture of amplified DNA molecules can be used as a sense primer to generate full-length DNA molecules of interest. This library of full-length DNA molecules can then be subjected to clonal isolation to obtain a single DNA molecule. Each cloned DNA molecule can then be sequenced, expressed, and characterized.

The present invention also contemplates compositions packaged as kits for producing recombinant host cells that express a fusion protein on the cell surface. As used herein, the term "package" refers to a solid matrix or material customarily utilized for a kit and capable of holding one or more of the reagent components for use in a method of the present invention. Packages can include containers, such as glass and plastic (e.g., polyethylene, polypropylene, polycarbonate, etc.) bottles, vials, paper, plastic and plastic-foil laminated envelopes, and the like.

A kit comprises at least one container comprising a nucleic acid molecule, which is a cell surface display expression cassette. An illustrative cell surface display expression cassette is a nucleic acid molecule, which comprises, in a 5' to 3' order: (1) a eukaryotic promoter, (2) a nucleotide sequence encoding a type II signal anchor domain, and (3) a cloning site. The expression cassette can also comprise a nucleotide sequence (located, for example, between the type II signal anchor domain and the cloning site) that encodes an affinity tag. Such expression cassettes can be included as a component of an expression vector.

The kit can also comprise a second container comprising one or more reagents capable of indicating the presence of an expressed fusion protein. For example, a container can comprise an antibody, or antibody fragment, which binds with an affinity tag. The antibody or antibody fragment can be detectably labeled, or a detectable label can be provided in another container. Additional containers can provide reagents for producing a cDNA library.

The reagents can be provided in solution, as a liquid dispersion or as a substantially dry powder. For example, nucleic acid molecules, antibodies, or antibody fragments can be provided in lyophilized form. A solid support and one or more buffers can also be included as separately packaged elements in this system.

A kit can also comprise a means for conveying to the user that the reagents are used to produce recombinant host cells expressing a fusion protein on the cell surface. The written material can be applied directly to a container, or the written material can be provided in the form of a packaging insert.

The present invention, thus generally described, will be understood more readily by reference to the following examples, which are provided by way of illustration and are not intended to be limiting of the present invention.

EXAMPLE 1

Cell Surface Display of Thrombopoietin

Thrombopoietin, a four-alpha-helix cytokine, was used to test the ability of the expression system to display complex, correctly folded, assembled proteins on the cell surface. The sequence encoding mature thrombopoietin was cloned as an EcoRI and XhoI fragment in surface display vector pSLBSDF2-1 in the correct reading frame to yield the plasmid pSLBSDF2-TPO. Following the transfection of pSLBSDF2-TPO into BHK570 or COS-1 cells, functional thrombopoietin was detected on the cell surface, as shown by specific binding with a horseradish peroxidase-labeled thrombopoietin receptor. Bound horseradish peroxidase was detected using the TSA-Direct kit, sold by NEN Life Science Products (Boston, Mass.). Briefly, adherent transfected cells were rinsed with phosphate-buffered saline to remove any autofluorescent particles, and the cells were incubated with diluted fluorescein tyramide for five minutes. The cells were then rinsed with phosphate-buffered saline to remove excess reagent, and the presence of activated fluorophor on cell surfaces was visualized with an inverted fluorescent microscope at a wavelength of 494 nm excitation/517 nm emission.

These studies included the use of three protocols prior to fluorescein tyramide treatment. In one protocol, cells were fixed with formaldehyde and treated with Triton-X to permeabilize cell membranes. To limit detection to the cell surface, a second protocol eliminated Triton-X treatment. In a third protocol, both fixation and permeabilization steps were omitted.

In addition to cells transfected with pSLBSDF2-TPO, another set of cells was transfected with a thrombopoietin expression plasmid, in which the type II signal anchor domain was replaced with a secretion leader. These cells exhibited thrombopoietin activity in the cell-conditioned media, but cell surfaces lacked any detectable binding of the thrombopoietin receptor.

The detection of functional thrombopoietin on the cell surface of transfected cells demonstrated that the display system is capable of producing correctly folded and assembled protein, and that the protein is tethered on the cell surface in a manner that can be recognized by a receptor.

EXAMPLE 2

Cell Surface Display of *Arabidoposis thaliana* Peroxidase

In another set of experiments, a transfection vector, designated as "pSLBSDF2-AP," was constructed to express *Arabidoposis thaliana* peroxidase. This enzyme is a plant peroxidase which requires a heme prosthetic group for activity. The sequence encoding the peroxidase was cloned as an EcoRI and XhoI fragment in surface display vector pSLBSDF2-1. Transfection of BHK 570 or COS-7 cells with pSLBSDF2-AP resulted in cells with cell surface peroxidase activity, as determined using the TSA-Direct kit, described above.

Cell surface deposition of activated fluorescein tyramide was not observed in expression vectors that were designed to secrete recombinant *Arabidoposis thaliana* peroxidase into the culture media. The detection of functional *Arabidoposis thaliana* peroxidase on the cell surface of pSLB-SDF2-AP-transfected cells showed that the display system is capable of producing correctly folded and assembled protein, and that the protein is tethered on the cell surface in a manner that can exhibit enzymatic activity.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

I claim:

1. An isolated nucleic acid molecule comprising (a) a eukaryotic promoter, (b) a nucleotide sequence encoding a type II signal anchor domain segment, (c) a nucleotide sequence that encodes a spacer peptide, and (d) a cloning site wherein the spacer peptide comprises SEQ ID NO: 1, and wherein the isolated nucleic acid molecule comprises elements (a) to (d) in a 5' to 3' order.

2. The isolated nucleic acid molecule of claim 1, further comprising a nucleotide sequence that encodes an affinity tag, wherein the affinity tag-encoding nucleotide sequence resides between the nucleotide sequence encoding the type II signal anchor domain segment and the cloning site.

3. The isolated nucleic acid molecule of claim 1, further comprising a nucleotide sequence that encodes an intron, wherein the intron-encoding nucleotide sequence resides between the promoter and the nucleotide sequence encoding the type II signal anchor domain segment.

4. The isolated nucleic acid molecule of claim 1, further comprising at least one sequence selected from the group consisting of (a) a translation termination sequence, (b) a polyadenylation signal sequence, and (c) a transcription termination sequence.

5. The isolated nucleic molecule of claim 4, comprising at least two of sequences (a) to (c), wherein the sequences reside in the following 5' to 3' order: translation termination sequence, polyadenylation signal sequence, and transcription termination sequence.

6. The isolated nucleic molecule of claim 5, comprising three sequences (a) to (c), wherein the sequences reside in the following 5' to 3' order: translation termination sequence, polyadenylation signal sequence, and transcription termination sequence.

7. An expression vector, comprising the isolated nucleic acid molecule of claim 1.

8. An isolated nucleic acid molecule, comprising (a) a eukaryotic promoter, (b) a nucleotide sequence encoding a type II signal anchor domain segment, (c) a nucleotide sequence that encodes a spacer peptide, and (d) a gene or gene fragment, wherein the isolated nucleic acid molecule comprises elements (a) to (d) in a 5' to 3' order, wherein the gene or gene fragment resides in-frame with the nucleotide sequence that encodes the type II signal anchor domain, wherein the spacer peptide comprises SEQ ID NO: 1, and wherein the nucleotide sequence that encodes a type II signal anchor domain segment is heterologous with respect to the gene or gene fragment.

9. An isolated nucleic acid molecule, consisting of (a) a eukaryotic promoter, (b) a nucleotide sequence encoding a type II signal anchor domain segment, (c) a nucleotide sequence that encodes a spacer peptide, and (d) a gene or gene fragment, wherein the isolated nucleic acid molecule comprises elements (a) to (d) in a 5' to 3' order, wherein the gene or gene fragment resides in-frame with the nucleotide sequence that encodes the type II signal anchor domain, wherein the spacer peptide comprises SEQ ID NO; 1, and wherein the nucleotide sequence that encodes a type II signal anchor domain segment is heterologous with respect to the gene or gene fragment.

10. The isolated nucleic acid molecule of claim 8, further comprising a translation termination sequence, which resides in a 3' position relative to the gene or gene fragment.

11. The isolated nucleic acid molecule of claim 10, wherein the translation termination sequence resides within the gene or gene fragment.

12. The isolated nucleic acid molecule of claim 11, further comprising a polyadenylation signal sequence, wherein the polyadenylation signal sequence is located 3' to the translation termination sequence.

13. The isolated nucleic acid molecule of claim 12, wherein the polyadenylation signal sequence resides within the gene or gene fragment.

14. The isolated nucleic acid molecule of claim 12, further comprising a transcription termination sequence, wherein the transcription termination sequence resides in a 3' position relative to the polyadenylation signal sequence.

15. The isolated nucleic acid molecule of claim 14, wherein the transcription termination sequence resides within the gene or gene fragment.

16. An expression vector, comprising the isolated nucleic acid molecule of claim 8.

17. The expression vector of claim 16, further comprising an affinity peptide encoding region.

18. The expression vector of claim 17, wherein the affinity peptide encoding region is located between the nucleotide sequence that encodes the type II signal anchor domain segment and the gene or gene fragment.

19. The expression vector of claim 16, further comprising a nucleotide sequence that encodes a spacer peptide, wherein the spacer peptide-encoding nucleotide sequence resides between the nucleotide sequence encoding the type II signal anchor domain segment and the gene or gene fragment, and wherein the spacer peptide comprises at least ten amino acids.

20. The expression vector of claim 16, further comprising at least one selectable marker gene.

21. The expression vector of claim 16, further comprising at least two origins of replication, wherein one origin of replication facilitates replication in an expression cell type, and wherein a second origin of replication facilitates replication in an amplification cell type, and wherein the expression cell type is eukaryotic and the amplification cell type is prokaryotic.

22. A recombinant host cell, comprising the expression vector of claim 16.

* * * * *

UNITED STATES PATENT AND TRADEMARK OFFICE
CERTIFICATE OF CORRECTION

PATENT NO. : 7,125,973 B2 Page 1 of 1
APPLICATION NO. : 10/693587
DATED : October 24, 2006
INVENTOR(S) : Si Lok It is certified that error appears in the above-identified patent and that said Letters Patent is hereby corrected as shown below:

Column 5, line 64, "tenninal" should read --terminal--.

Signed and Sealed this

Sixth Day of March, 2007

JON W. DUDAS
*Director of the United States Patent and Trademark Office*